US012778533B2

(12) United States Patent
Wang et al.

(10) Patent No.: US 12,778,533 B2
(45) Date of Patent: Nov. 3, 2026

(54) GATED BREATHING RADIOGRAPHIC TRIGGER

(71) Applicant: CARESTREAM HEALTH, INC., Rochester, NY (US)

(72) Inventors: Xiaohui Wang, Pittsford, NY (US); Luca Bogoni, Philadelphia, PA (US); Robert S. Jones, Rochester, NY (US); Charles W. Hicks, Rochester, NY (US)

(73) Assignee: Carestream Health, Inc., Rochester, NY (US)

(*) Notice: Subject to any disclaimer, the term of this patent is extended or adjusted under 35 U.S.C. 154(b) by 197 days.

(21) Appl. No.: 18/705,716

(22) PCT Filed: Nov. 16, 2022

(86) PCT No.: PCT/US2022/050070

§ 371 (c)(1),
(2) Date: Apr. 29, 2024

(87) PCT Pub. No.: WO2023/096798

PCT Pub. Date: Jun. 1, 2023

(65) Prior Publication Data

US 2026/0157719 A1 Jun. 11, 2026

Related U.S. Application Data

(60) Provisional application No. 63/283,663, filed on Nov. 29, 2021.

(51) Int. Cl.
*A61B 6/00* (2024.01)

(52) U.S. Cl.
CPC .................................... *A61B 6/541* (2013.01)

(58) Field of Classification Search
CPC .. A61B 6/56; A61B 5/11; A61B 6/541; G06T 7/73; G01S 17/89
See application file for complete search history.

(56) References Cited

U.S. PATENT DOCUMENTS

2010/0166145 A1* 7/2010 Umekawa .............. A61B 6/541 378/65
2015/0094606 A1* 4/2015 Mestha ................ A61B 5/7282 600/534

(Continued)

FOREIGN PATENT DOCUMENTS

EP 3 838 157 A1 6/2021
EP 3 882 921 A1 9/2021

(Continued)

OTHER PUBLICATIONS

International Search Report mailed on Mar. 24, 2023 for International Application No. PCT/US2022/050070, 3 pages.

(Continued)

*Primary Examiner* — Courtney D Thomas
(74) *Attorney, Agent, or Firm* — Eugene I Shkurko

(57) ABSTRACT

A method of activating an x-ray source includes monitoring a patient's breathing using a depth camera aimed at the patient and detecting cyclical peaks in depth data provided by the depth camera. The x-ray source is activated at a predetermined time based on the detected cyclical peaks in order to capture a radiographic image of the patient at a peak inhalation time.

15 Claims, 4 Drawing Sheets

(56) References Cited

U.S. PATENT DOCUMENTS

| | | | | |
|---|---|---|---|---|
| 2019/0374189 | A1 | 12/2019 | Kiely | |
| 2020/0202620 | A1* | 6/2020 | Kiely | A61B 6/541 |
| 2020/0352524 | A1 | 11/2020 | Hu et al. | |

FOREIGN PATENT DOCUMENTS

| | | |
|---|---|---|
| JP | 2014-204932 | 10/2014 |
| WO | 2021/258155 | 12/2021 |

OTHER PUBLICATIONS

NPL, Quoc-Viet Trans et al., "Pyramidal Lucas-Kanade-Based Noncontact Breath Motion Detection," IEEE Transactions on Systems, Man, and Cybernetics Systems, vol. 50, No. 7, Jul. 2020, pp. 2659-2670.

* cited by examiner

GATED BREATHING RADIOGRAPHIC TRIGGER

CROSS REFERENCE TO RELATED APPLICATIONS

This application claims the benefit of and is a U.S. National Phase filing of PCT Application PCT/US2022/050070 filed Nov. 16, 2022 entitled "GATED BREATHING RADIOGRAPHIC TRIGGER", in the name of Wang et al., which claims benefit of U.S. Patent Application Ser. No. 63/283,663, filed Nov. 29, 2021, in the name of Wang et al., and entitled GATED BREATHING RADIOGRAPHIC TRIGGER.

The subject matter disclosed herein relates to chest x-ray imaging. In particular, to methods and apparatus for detecting patient breathing cycles and automatically synchronizing activation of an x-ray source with a patient's breathing cycle.

For optimal interpretation by a radiologist, chest radiographs are typically acquired in the inspiratory phase of the respiratory cycle. The x-ray technologist requests the patient to breathe in and, upon reaching full inspiration, hold their breath. Patients having difficulty breathing, or who are sedated, may find this difficult if not impossible. For example, ventilated patients in an intensive care unit are unable to follow such instructions. The x-ray technologist can manually synchronize the acquisition by pressing the inspiratory hold button on the ventilator, but this requires them to be near the patient to be able to monitor their breathing and would therefore need to wear a lead apron. Furthermore, in the event of contagious patients, this adds additional degrees of difficulty as appropriate protective gear would have to be worn. To overcome this burden to workflow, it is therefore desirable to develop an automated process to synchronize a patient's breathing cycle to the acquisition of a chest x-ray.

The discussion above is merely provided for general background information and is not intended to be used as an aid in determining the scope of the claimed subject matter.

BRIEF DESCRIPTION OF THE INVENTION

A method and apparatus for activating an x-ray source includes monitoring a patient's breathing using a depth camera aimed at the patient and detecting cyclical peaks in depth data provided by the depth camera. The x-ray source is activated at a predetermined time based on the detected cyclical peaks in order to capture a radiographic image of the patient at a peak inhalation time.

In one embodiment, a radiographic imaging system with an x-ray source and a digital radiographic detector also includes a camera system. The camera system may include a depth camera that is aimed at a patient who will be radiographically imaged and provides depth data that is used to determine the patient's breathing cycles. A processing system is configured to detect cyclical peaks in the depth data and to fire the x-ray source at least once based on the timing of the cyclical peaks.

In one embodiment, a method of activating an x-ray source includes monitoring a patient's breathing using a depth camera aimed at the patient and collecting depth data from the depth camera. Cyclical peaks in the depth data provided by the depth camera are monitored by a processing system and the x-ray is activated at a predetermined time based on the detected breathing cycles.

Disclosed herein is a solution whereby a camera system is used to detect the breathing cycles of a patient. A camera system having one or more cameras may be mounted on the x-ray tube head and positioned to view the patient's chest region. One camera type may be a depth camera, or it may include a LIDAR (light detection and ranging) equipped camera, or it may include an infra-red camera, or it may include a video camera, to measure the variation of depth of the patient's chest as the patient breathes. In one embodiment, other suitable distance measuring devices may be used and configured to communicate with a radiographic imaging system as described herein. For example, devices using radio frequency waves, acoustic waves, or other technologies may be used to measure a patient's breathing cycles. A region on the patient's chest is selected which can be used to accurately measure the breathing cycle by using the camera's sensor within this region of interest. Whereas the present description of the invention may provide an embodiment wherein a camera system is mounted on the x-ray tube head, without loss of generality the camera system may also be mounted on the ceiling of an x-ray facility or it may be free standing, so long as it has a view of the chest of the patient to be able to implement the depth monitoring.

A LIDAR equipped camera, or an infra-red camera, or a laser emitting camera, may configured to emit pulsed light waves at a rate of multiple times per second toward the patient, which pulses reflect from the patient's chest area and return to the camera's LIDAR, infra-red, or laser sensor. The sensor measures the round-trip time, or time-of-flight, for each pulse and calculates the precise distance that the light pulse traveled. Repeating this process millions of times per second may be used to create a precise, real-time graph of the patient's breathing cycle. Such data can be used to determine inhalation peaks in the patient's breathing cycle, measure a time between inhalation peaks (cycle time), and then trigger an x-ray source to expose the patient at maximum inhalation in order to capture a radiographic image of the patient's chest at the instant of maximum inhalation.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the coverage of the claims below, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This application claims priority to U.S. Patent Application Ser. No. 63/283,663, filed Nov. 29, 2021, in the name of Wang et al., and entitled GATED BREATHING RADIOGRAPHIC TRIGGER, which is hereby incorporated by reference herein in its entirety.

Figure 1:
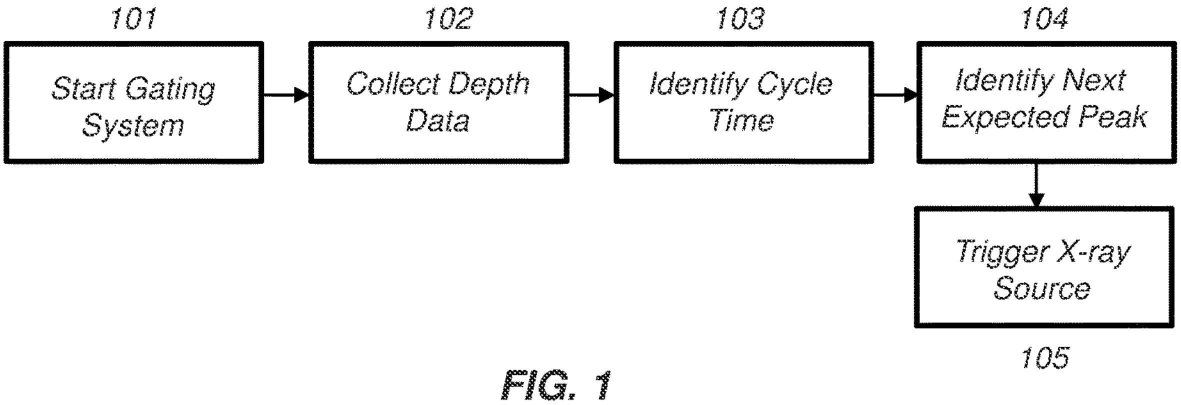
FIG. 1 is a flow diagram of an exemplary respiratory gating process used to trigger an x-ray source.
Figure 2:
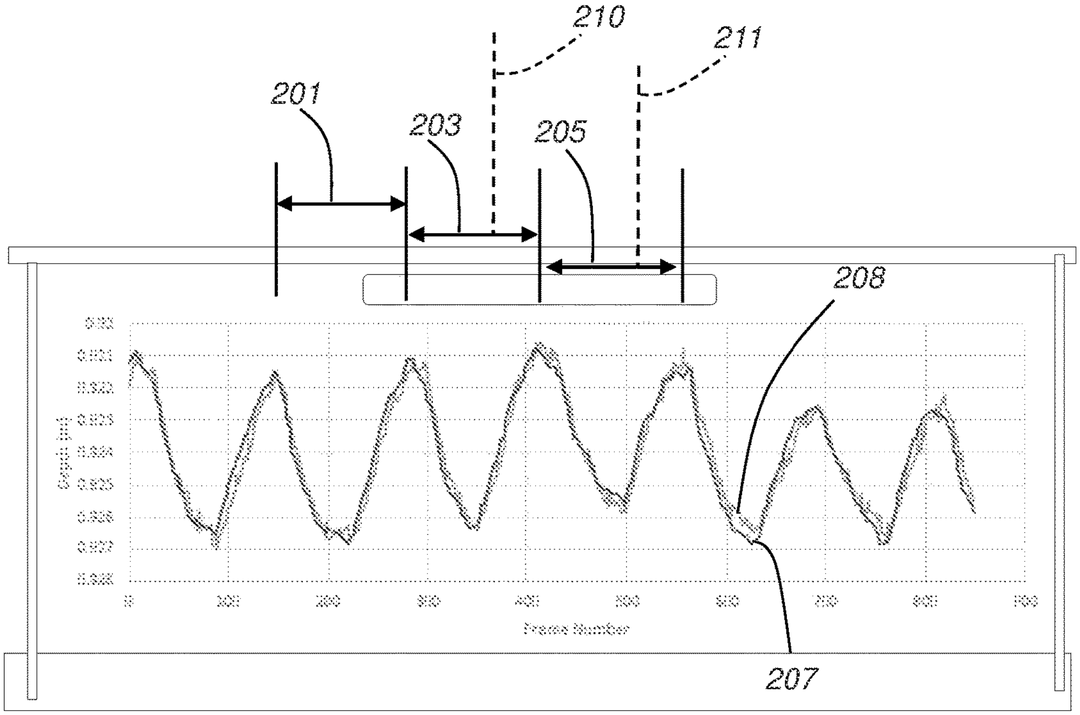
FIG. 2 is a graph illustrating camera and laser detections of a patient breathing cycle.

FIG. 1 is a flow diagram illustrating an exemplary embodiment of the present invention. In step 101 the gating system of the present invention is activated. The gating system may include a depth camera aimed at a patient's chest to measure the patient's breathing cycles, or the camera may include a pulsed light source, such as a laser light source, an infra-red (IR) light source, or other suitable light source, whose reflections from the patient chest is detected and are used to measure a time-of-flight of the emitted light pulse and to calculate a distance from the camera to the patient chest. In one embodiment, one or more IR reflective patches may be strategically placed on the patient's chest region to increase reflectivity of the emitted light. The light source may be configured to emit a light pulse every n seconds, where n may be selectively configured to range from about 0.1 s to $1\times10^{-7}$ s, although a value of n ranging from about 0.1 s to about 0.01 s may be satisfactory for the purposes described herein. In step 102, a series of data points may thus be digitally generated and collected by the gating system, and plotted such as shown in the graph of FIG. 2. In step 103, the patient's breathing cycle times, e.g., 201, 203, 205, of FIG. 2, may be calculated, and stored at least temporarily. In response to an x-ray system operator activating the x-ray source, at step 104 a time of the next expected breathing cycle peak (maximum inhalation) is calculated and, at step 105, the x-ray source is triggered at the calculated time.

With reference to FIG. 2, cyclical peaks can be seen in the graph relative to the beginning of cycles 201, 203, 205, for example. The horizontal axis represents the light pulse number (consecutively numbered as "frames") which is emitted at regular time intervals as described herein, while the vertical axis represents the measured distance from the camera to the patient chest, in units of meters. One of the plots 207 corresponds to measurements/detections made using a laser source as described herein. Another one of the plots 208 corresponds to measurements made using a commonly available depth camera. The laser signal was used to compare against the depth camera data during breathing experiments. Applicants have used this data to verify that the measurements using these different camera system technologies are closely matched.

Table 1 lists an exemplary portion of the data points collected by the gating system and used to plot the graph 207 as shown in FIG. 2. A processing system may be programmably configured to determine local cyclical peaks using the data of Table 1 and as represented in FIG. 2. As shown in the portion of depth data illustrated in Table 1, frame numbers 150 and 280, for example, can be programmably identified as local cyclical peaks in the patient's measured breathing cycle, which correspond to the beginning of cycle 201 and cycle 203 in FIG. 2, respectively. Multiplying the number of frames in the cycle 201 (280−150=130) by the configured value n, described above, provides the cycle time 201 in units of seconds; or the cycle time may be conveyed in numbers of frames, such as one hundred thirty (130) light pulses.

TABLE 1

| Frame # | Meters |
|---|---|
| . . . | . . . |
| 149 | 0.9220 |
| 150 | 0.9215 |
| 151 | 0.9218 |
| . . . | . . . |
| 279 | 0.9215 |
| 280 | 0.9211 |
| 281 | 0.9214 |
| . . . | . . . |

In one embodiment, if an operator of the radiographic imaging system initiates an image capture at a time 210 to capture an image of the patient's chest whose breathing cycle is shown in FIG. 2, the imaging system may be programmed to use the calculated cycle time 201 to schedule firing the x-ray source at a time determined by adding the cycle time 201 to the time at the end of cycle 201, which is expected to correspond closely with the end of cycle time 203 (maximum inhalation) due to the patient breathing rate remaining suitably constant. Similarly, if an operator of the system initiates an image capture at a time 211 to capture an image of the patient's chest whose breathing cycle is shown in FIG. 2, the imaging system may be programmed to use the calculated cycle time 201, or the calculated cycle time 203, or an average of the cycles times 201 and 203, or an average of any desired number of previous cycle times, to schedule firing the x-ray source at a time determined by adding the desired calculated cycle time to the time at the end of cycle 203, which is expected to correspond closely with the end of cycle time 205 (maximum inhalation) due to the patient breathing rate remaining suitably constant. Similarly, at about frame 550, corresponding to the end of cycle time 205 which is the expected next peak cycle time after the end of cycle time 203. The imaging system may be programmed as desired, such as to delay firing the x-ray source until a second or third cyclical peak occurs after the operator initiates an image capture, or any other time. In another embodiment, if an operator of the radiographic imaging system initiates an image capture at a time 210 to capture an image of the patient's chest whose breathing cycle is shown in FIG. 2, the imaging system may be programmed to use the total frames (light pulses) in the calculated cycle time 201 to schedule firing the x-ray source at a time synchronized with a light pulse number determined by adding the frames of cycle time 201 (frame≈130) to the time at the end of cycle 201 (frame≈280), which is expected to correspond closely with the end of cycle time 203 (frame≈410, maximum inhalation) due to the patient breathing rate remaining suitably constant. Depending on a physical condition of the patient, a breathing cycle may vary widely, but typically may be expected to vary from about two (2) seconds to about five (5) seconds.

Figure 3A:
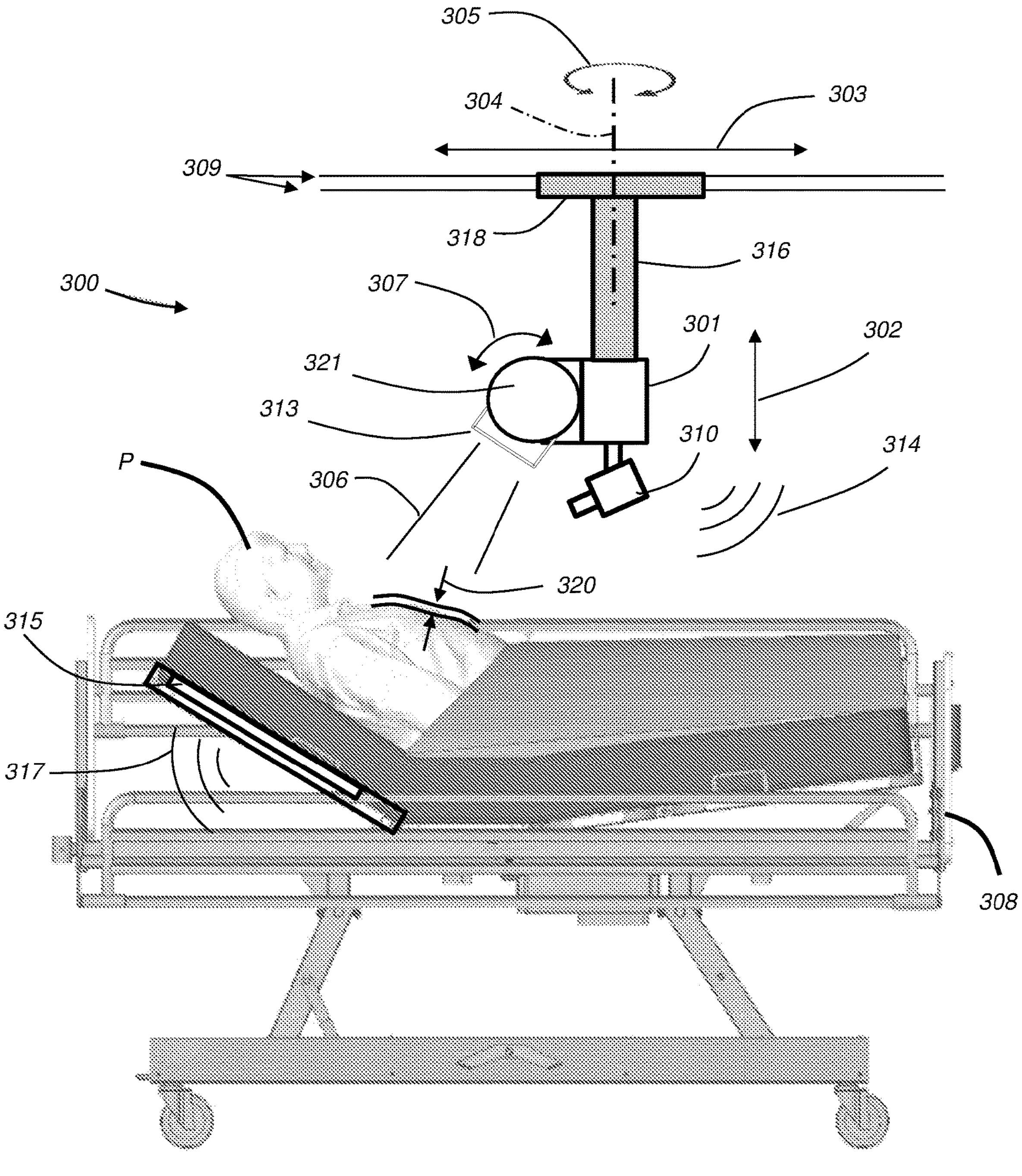
FIGS. 3A-3B are schematic views of a radiographic imaging system for automatically timing x-ray source activation.
Figure 4:
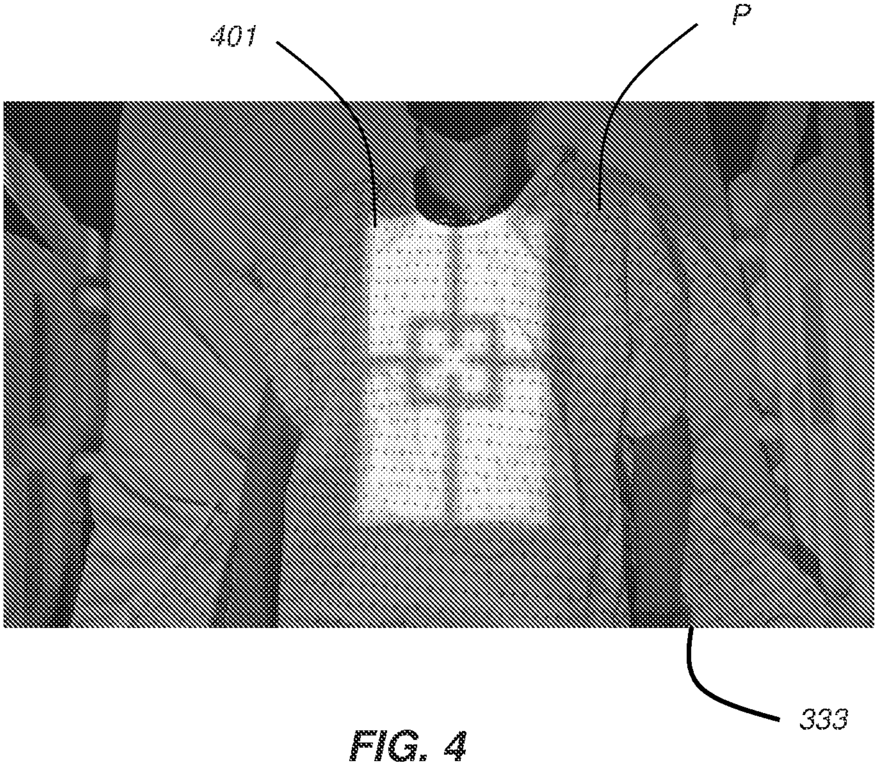
FIG. 4 illustrates positioning of the gating and imaging system.

FIG. 3A is a schematic diagram of an exemplary radiographic imaging system 300 that may be deployed in medical imaging facilities. A movable tube head 301 includes an x-ray source 321, and has a collimator 313 attached thereto, which tube head 301 may be mounted on an overhead tube crane that includes an extendable vertical support column 316, to which the tube head 301 is attached, and a movable crane base 318, to which the extendable vertical support column 316 is attached. The movable crane base 318 is attached to crane tracks 309 which are affixed to a ceiling of the patient room. When the crane base 318 is moved along the crane tracks 309, such as by a remote controllable motor drive, the tube head 301 may be moved to a desired position. The collimator 313 may include an electronically controlled aperture having four individually movable blades for controlling a size of a rectangular aperture which, in turn, controls dimensions of an x-ray beam 306 emitted by the x-ray source 321 and may also control an illumination region of a collimator light projected onto the patient P (FIG. 4). The crane base 318 may also be attached to second transverse tracks (not shown) to allow remote controlled movement of the tube head 301 in a transverse direction, relative to crane tracks 309, along the ceiling. Typically, the overhead crane base 318 movements may be configured to be perpendicular to each other and both parallel to a ceiling of the patient room containing the radiographic imaging system. The extendable vertical support column 316 may also be configured to be telescopically extendable and retractable vertically along directions 302. The crane base 318 includes an electric motor for controllably driving the crane base 318 along the tracks 309. Movement of the overhead tube crane allows controlled positioning of the tube head 301 in relation to the patient P and the DR detector 315 located behind the patient P. After controllably positioning the tube head 301 in relation to DR detector 315, for example, the x-ray source 321 therewithin may be remotely and controllably fired to emit x-ray beam 306 to capture a radiographic image of the chest of the patient P, lying on the patient bed 308, in the DR detector 315. As described in detail herein, such positioning of the tube head 301 and initiating x-ray exposures may be performed automatically without requiring personnel to be present in the patient room. In one alternative embodiment, tube head 301 may include a plurality of x-ray sources such as carbon nanotubes or other cold cathode sources.

Figure 3B:
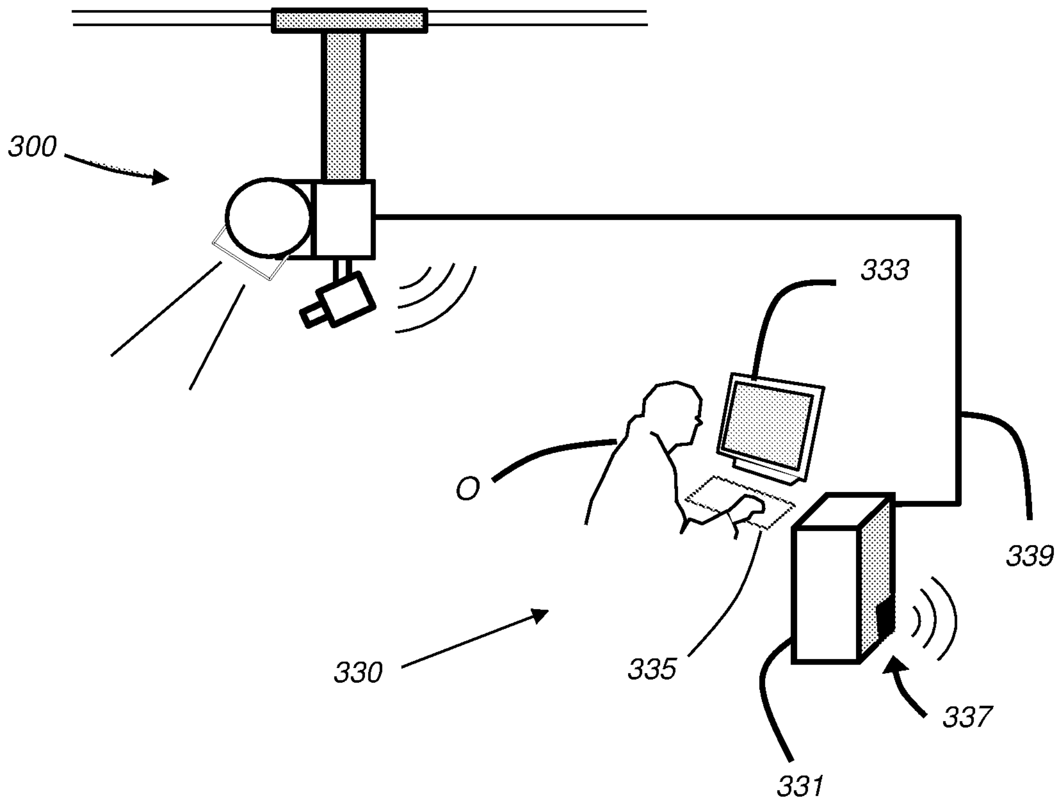

Referring to FIGS. 3A-3B, an operator control console 330 may include a processing system 331 for remotely controlling operation of the radiographic imaging system 300 described herein. The processing system 331 may include a wired coupling 339 or a wireless transmission capability via transceiver 337 for communicating with and controlling movement and operation of the imaging system 300, such as a power level and/or firing sequence of the x-ray source(s) 321, and timing of x-ray source 321 firing to capture images of patient P in DR detector 315. The tube head 301 and digital camera system 310 may include a wireless communication capability 314, and the digital detector 315 may also include wireless communication capability 317, respectively, for exchanging data and receiving commands and instructions from operator control console 330. The control console 330 includes connected I/O devices such as a keyboard/mouse 335 and a digital display 333 for operator O use. The control console 330 may communicate wirelessly with DR detector 315 to receive captured radiographic images transmitted to the control console 330, and for timing activation of the x-ray source 321 as described herein. The control console 330 may then transmit captured radiographic images to other network connected devices over a wired or wireless channel, such as to hand held tablets and cell phones. The control console 330 may be electronically connected to a medical facility communication network where the radiographic imaging system is installed.

The control console 330 may be located remotely from the patient room to provide an environment for operator O that is isolated from the patient room. The control console 330 may be used by operator O to obtain radiographic images of a patient P in the patient room without requiring operator O to have a direct line of sight of the patient P. The control console 330 may be located in a control room of a medical facility adjacent or remote from the patient room 102. In a separate embodiment, the control system 330 may be configured and located at a particular site so that operator O may have a line of sight view of the patient P on the patient bed 308, such as by providing a window through which the operator O can directly view the patient P.

As shown in FIGS. 3A-3B, tube head 301, having an x-ray source, or sources, therein and a collimator 313 attached thereto, is mounted on extendible vertical support column 316 which, in turn, is attached to crane base 318 that is configured to move along crane tracks 309. Alternatively, the camera system 310 may be mounted on a wall of the patient room. The tube head 301 may be controlled by control console 330 to: (a) move vertically in directions 302 using telescoping extendible vertical support column 316; (b) move horizontally in directions 303 using crane base 318 movement along crane tracks 309; and (c) rotate about vertical axis 304 in directions 305. Similarly, tube head 301 and collimator 313 may be rotated in directions 307 to emit an x-ray beam 306 at a desired angle. The tube head 301 may be positioned so as to align the x-ray beam 306 with the DR detector 315 positioned behind patient P.

To properly position the tube head 301, the operator O may make use of a live video digital camera as part of the camera system 310 attached, for example, to tube head 301 and aimed at patient P. As shown in FIG. 4, the video camera portion of camera system 310 may capture and transmit a live video image of the patient P for display to an operator O on digital display 333. As shown in FIG. 4, the collimator light may be activated by operator P which illuminates a region 401 of the chest the patient P and is recognized by viewing the live video image displayed on the digital display 333. As used herein, the term gating system refers to both the imaging system 300 and control console 330 described herein. Referring back to step 101 of FIG. 1, the depth camera portion of the camera system 310, may be activated by the operator O at control console 330, i.e., activating the gating system, by using the depth camera aimed toward a center of the region 401 of the chest of patient P illuminated by the collimator light. The depth camera data is collected under control of the processing system 331 as exemplified by the data portion shown in Table 1 together with identifying cycle times as described herein. The depth camera data includes timed measurements of the varying distance 320 (FIG. 3A) of a surface of the chest of a breathing patient P relative to the measurement camera in camera system 310. Upon image capture initiation requested by operator O at the control console 330, as described herein, the processing system 331 will selectively determine the expected breathing cycle peak time for programmed image capture and trigger the x-ray source 321 at the determined time to capture a radiographic image of the chest of patient P.

In one embodiment, the processing system 331 may store known system latency information, which corresponds to a delay time as between triggering the x-ray source 321 and an actual emission of an x-rays 306 from the x-ray source 321. The processing system 331 may be configured to incorporate such latency data to adjust a timing of a trigger signal transmitted to the x-ray source 321 in order for the x-ray source 321 to emit x-rays at a desired instant.

FIG. 4 shows an illuminated region 401 of the patient P using the collimator light that is cast from the collimator 313 during operator alignment of the tube head 301 to the patient's chest region using the video captured by a video camera in camera system 310 and displayed to an operator O on display 333. The projected lighted region indicates the area of the chest that is of most interest in determining the respiratory gating and imaging of the patient.

It is understood that alternative methods to determine depth data, such as stereo, or structured lighting (whether visible or IR) may be used. The ability to perform a breathing peak expectation may also incorporate information from other devices in the ICU room or patient bedside at the time of the acquisition, such as breathing tubes or other monitors to create a more robust prediction. Additionally, prior breathing cycles for the specific patient, may be available from prior acquisitions and thus may be used as a means to generate more robust assessment of peak estimation.

In order to increase the robustness of breathing peak prediction, the breathing cycles of a patient may be aggregated with breathing cycles of other patients. This aggregation may include other sources of data such as imaging, prior clinical exams, demographics etc. Additionally, it may incorporate information from other devices at the patient bedside. As a result, such an aggregation may be used to create classes of breathing models for a cluster of patients. Thus, these models may be available at the time of a patient exam to fit the newly acquired data and generate a better prediction of the breathing model and thus the best breathing peak.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The invention claimed is:

1. A radiographic imaging system comprising:

an x-ray source;

a radiographic detector for recording a radiographic image of a patient exposed by the x-ray source;

a camera for measuring varying depth and providing varying depth data, wherein the varying depth is a varying distance between the camera and a region of the patient exposed by the x-ray source; and a processing system for controlling the radiographic imaging system and for receiving the varying depth data from the camera, the processing system configured to detect cyclical peaks in the varying depth data, to calculate a future time of a subsequent cyclical peak, and to fire the x-ray source at the calculated future time.

2. The system of claim 1, wherein the varying depth data corresponds to a chest region of the patient while the patient is breathing.

3. The system of claim 1, wherein the imaging system comprises a tube head containing the x-ray source and wherein the camera is attached to the tube head.

4. The system of claim 1, wherein the processing system is configured to determine a cycle time between the cyclical peaks, and wherein the processing system is configured to fire the x-ray source at the determined cycle time after a most recent detected cyclical peak.

5. The system of claim 4, wherein the processing system is configured to calculate the future time of the subsequent cyclical peak based on the determined cycle time between the cyclical peaks.

6. The system of claim 1, further comprising a second depth camera, wherein the varying depth data comprises data obtained from multiple depth cameras.

7. The system of claim 1, wherein the processing system is further configured to fire the x-ray source at least once based on a preselected time difference in relation to one or more of the detected cyclical peaks.

8. The system of claim 1, wherein the processing system is further configured to calculate a system latency and to control firing the x-ray source at the calculated future time based on the system latency.

9. The system of claim 1, wherein the processing system is configured to calculate the future time within about 0.1 to about 0.01 seconds.

10. A method of activating an x-ray source, the method comprising:

monitoring a patient's breathing using a camera aimed at the patient and collecting varying depth data from the camera;

detecting cyclical peaks in the varying depth data provided by the camera;

calculating a cycle time between the detected cyclical peaks;

calculating a future time of a subsequent cyclical peak based on the calculated cycle time; and activating the x-ray source at the calculated future time.

11. The method of claim 10, further comprising activating the x-ray source at least once in synchrony with at least one expected cyclical peak.

12. The method of claim 10, further comprising activating the x-ray source at least once at a preselected time difference in relation to at least one of the detected cyclical peaks.

13. The method of claim 10, wherein the step of calculating a cycle time includes measuring an elapsed time between at least one pair of previously occurring consecutive cyclical peaks.

14. The method of claim 13, wherein the step of calculating a cycle time includes calculating an average elapsed time between at least two pairs of previously occurring consecutive cyclical peaks.

15. The method of claim 10, further comprising calculating the future time of the subsequent cyclical peak to within about 0.1 to about 0.01 seconds.

* * * * *